(12) United States Patent     (10) Patent No.:    US 8,642,069 B2
Goldin     (45) Date of Patent:    Feb. 4, 2014

(54) COMPOSITION AND METHOD FOR TREATING COLDS

(76) Inventor: Alexander D. Goldin, Glenview, IL (US)

( * ) Notice: Subject to any disclaimer, the term of this patent is extended or adjusted under 35 U.S.C. 154(b) by 574 days.

(21) Appl. No.: 12/548,835

(22) Filed: Aug. 27, 2009

(65)     Prior Publication Data

US 2010/0055046 A1     Mar. 4, 2010

Related U.S. Application Data

(60) Provisional application No. 61/092,126, filed on Aug. 27, 2008, provisional application No. 61/120,532, filed on Dec. 8, 2008.

(51) Int. Cl.
    *A61K 9/00*        (2006.01)
    *A61K 9/08*        (2006.01)
    *A61K 31/00*      (2006.01)
    *A61K 31/56*      (2006.01)
    *A61K 31/35*      (2006.01)

(52) U.S. Cl.
    USPC .............. 424/434; 424/45; 514/171; 514/178

(58) Field of Classification Search
    USPC .............................. 424/434, 45; 514/171, 178
    See application file for complete search history.

(56)     References Cited

U.S. PATENT DOCUMENTS

| | | | |
|---|---|---|---|
| 4,335,121 A | 6/1982 | Phillipps et al. | |
| 5,116,863 A | 5/1992 | Oshima et al. | |
| 5,164,194 A | 11/1992 | Hettche | |
| 5,837,699 A | 11/1998 | Sequeira et al. | |
| 6,127,353 A | 10/2000 | Yuen et al. | |
| 6,723,713 B2 | 4/2004 | Sequeira et al. | |
| 6,858,596 B2 | 2/2005 | Biggadike et al. | |
| 7,101,866 B2 | 9/2006 | Biggadike et al. | |
| 7,959,597 B2 * | 6/2011 | Baker et al. ...................... | 604/28 |
| 2006/0110405 A1 * | 5/2006 | Buckheit, Jr. ............... | 424/204.1 |
| 2006/0205682 A1 | 9/2006 | Roberts et al. | |
| 2006/0228306 A1 * | 10/2006 | Lane ............................... | 424/45 |
| 2007/0202050 A1 * | 8/2007 | Berry et al. ...................... | 424/45 |
| 2008/0146606 A1 | 6/2008 | Bamborough et al. | |

OTHER PUBLICATIONS

Flonase nasal spray, Jul. 2003, from PDR Electronic Library (Obtained Dec. 3, 2011).*
Plyush et al, An assessment of the onset and duration of action of olopatadine nasal spray, Otolaryngology-Head and Neck Surgery, Dec. 2007, vol. 137, No. 6.*
Wong et al, Guidelines for the use of antibiotics in acute upper respiratory tract infections, American Family Physician, vol. 74, No. 6, Sep. 15, 2006.*
Nonallergic Rhinitis, http://www.MayoClinic.com/health/nonallergic-rhinitis/DS00809 (last visited Apr. 9, 2012).
Rhinitis (Hay Fever): Tips to Remember, American Academy of Allergy Asthma & Immunology, http://www.aaaai.org/conditions-and-treatments/library/at-a-glance/rhinitis.aspx (last visited Apr. 9, 2012).
Proud et al., Gene Expression Profiles during in Vivo Human Rhinovirus Infection, Am J Respir Crit Care Med, vol. 178, pp. 962-968 (2008).
Qvarnberg et al., Intranasal beclomethasone dipropionate in the treatment of common cold, Rhinology, vol. 39, pp. 9-12 (2001).
Puhakka et al., The common cold: Effects of intranasal fluticasone propionate treatment, J Allergy Clin Immunol, vol. 101, No. 6, pp. 726-731(1998).
The Common Cold: Rhinitis Vs. Sinusitis: Physician Information Sheet (Pediatrics), http://www.cdc.gov/getsmart/campaign-materials/info-sheets/child-rhin-vs-sinus.html (last visited Apr. 4, 2009).
Slavin et al., The diagnosis and management of sinusitis: A practice parameter update, J Allergy Clin Immunol, vol. 116, No. 6, pp. S13-S47 (2005).
Weida, A tool for Evaluating Patients with Cold Symptoms, Fam Pract Manag., vol. 11, No. 9, p. 53 (2004).
Quillen et al., Diagnosing Rhinitis: Allergic vs. Nonallergic, American Family Physician, vol. 73, No. 9, pp. 1583-1590 (2006).
Stillman, ACAAI 2011: Guidelines for the Diagnosis and Management of Sinusitis/Rhinosinusitis, Part 1, http://www.hcplive.com/conferences/acaai-2011/guidelines-for-the-diagnosis-and-management-of-sinusitis-rhinosinusitis-part-1 (last visited Apr. 5, 2011).
Stillman, ACAAI 2011: Guidelines for the Diagnosis and Management of Sinusitis/Rhinosinusitis, Part 2, http://www.hcplive.com/conferences/acaai-2011/guidelines-for-the-diagnosis-and-management-of-sinusitis-rhinosinusitis-part-2 (last visited Apr. 5, 2011).
Lubbe, Rhinosinusitis: management guidelines, CME, vol. 27, No. 8, pp. 349-352 (2009).
Wallace et al., The diagnosis and management of rhinitis: An updated practice parameter, J Allergy Clin Immunol, vol. 122, No. 2, pp. S1-S84 (2008).

* cited by examiner

*Primary Examiner* — Mina Haghighatian
(74) *Attorney, Agent, or Firm* — Schiff Hardin LLP

(57)     ABSTRACT

Viral upper respiratory tract infections, upper respiratory infections, and common colds can be effectively treated by the administration of a combination of a nasal steroid and a nasal antihistamine. By the administration of the combination of a nasal steroid and a nasal antihistamine with the onset of cold symptoms, the histamine cascade and the inflammatory response are impeded or eliminated, reducing the severity, duration, or frequency of the onset of cold symptoms. The combination of a nasal steroid and a nasal antihistamine may be, for example, a physical mixture of the steroid and antihistamine, or it may effectively be a combination wherein the patient is administered one component (either the steroid or the antihistamine) followed by the other, without physical mixing beforehand.

20 Claims, 8 Drawing Sheets

US 8,642,069 B2

COMPOSITION AND METHOD FOR TREATING COLDS

CROSS-REFERENCE TO RELATED APPLICATION

This application claims the benefit of U.S. Provisional Patent Application Ser. No. 61/092,126, filed Aug. 27, 2008 and U.S. Provisional Patent Application Ser. No. 61/120,532, filed Dec. 8, 2008.

BACKGROUND

1. Technical Field

This invention relates to products and methods for treating viral respiratory tract infections ("VRTIs") and upper respiratory infections ("URI"), both of which are otherwise known as the common cold. For the purposes of this disclosure, the terms "cold," "VRTI," and "URI" are used interchangeably. There is a desire to provide a better treatment for VRTIs, URIs, and common colds.

2. Description of the Related Art

Common colds are among the most common infectious diseases, causing millions of doctor visits at a cost of billions of dollars each year. As a VRTI, URI, or cold begins, the person experiences symptoms such as nasal congestion, sneezing, bronchial congestion, watery eyes, headaches, runny nose and a host of other varying symptoms, all of which are well known. As used in the present disclosure, these symptoms are collectively referred to as "cold symptoms" or the "inflammatory response." Typically, cold symptoms are caused by some type of picornavirus (usually a rhinovirus), coronavirus, or respiratory syncytial virus ("RSV"). Current treatments for VRTIs, URIs, and colds are palliative, focusing on reducing the severity of the symptoms of the VRTI. Although current treatments are intended to reduce the severity of cold symptoms, current treatments do not claim to reduce the cold's duration or to reduce the frequency with which a person experiences colds (e.g., VRTIs or URIs) or cold symptoms.

One aspect of the present invention is a combination of a nasal steroid with a nasal antihistamine, and the use of that combination in the treatment of VRTIs, URIs, or colds. Nasal steroids or antihistamines have been used in the art to treat rhinitis associated with common allergies, but they have not been used together to treat VRTIs, URIs, or colds.

Steroid treatment of rhinitis works by blocking the inflammatory response by decreasing the influx of mast cells, Th2 lymphocytes, and eosinophils. The mechanism by which steroid applications address upper respiratory inflammation is known in the art. See, e.g., U.S. Pat. No. 7,101,866 (filed Aug. 3, 2001); U.S. Pat. No. 6,858,596 (filed Feb. 4, 2002); U.S. Pat. No. 6,723,713 (filed Apr. 30, 2003); U.S. Pat. No. 6,127,353 (filed Apr. 29, 1998); U.S. Pat. No. 5,837,699 (filed Mar. 20, 1997); see generally U.S. Pat. No. 4,335,121 (filed Feb. 13, 1981), which are incorporated by reference in their entirety.

Antihistamine treatments of rhinitis operate by inhibiting the release or activity of histamines via a selective inhibition of H1 receptors. The mechanism by which various antihistamines address upper respiratory inflammation is known in the art. See, e.g., U.S. Pat. No. 5,164,194 (filed Jul. 12, 1990); U.S. Pat. No. 5,166,863 (filed Mar. 2, 1987), which are incorporated by reference in their entirety.

Heretofore, nasal steroids and nasal antihistamines have been used individually or in combination to treat persons suffering from the effects of allergies, but not to treat persons suffering from VRTIs, URIs, or colds. One aspect of the present invention is the use of the combination of nasal steroids with nasal antihistamines, such as for example in a nasal spray, for the treatment of the common cold.

BRIEF DESCRIPTION

One aspect of the present invention is a combination for treating viral respiratory tract infections comprising one or more nasal steroids and one or more nasal antihistamines. Another aspect of the present invention is a method of treating a viral respiratory tract infection comprising administering an effective amount of a nasal antihistamine and a nasal steroid. Another aspect of the present invention is a method of preventing the onset of a viral respiratory tract infection comprising administering an effective amount of a nasal antihistamine and a nasal steroid.

DETAILED DESCRIPTION

Figure 1:
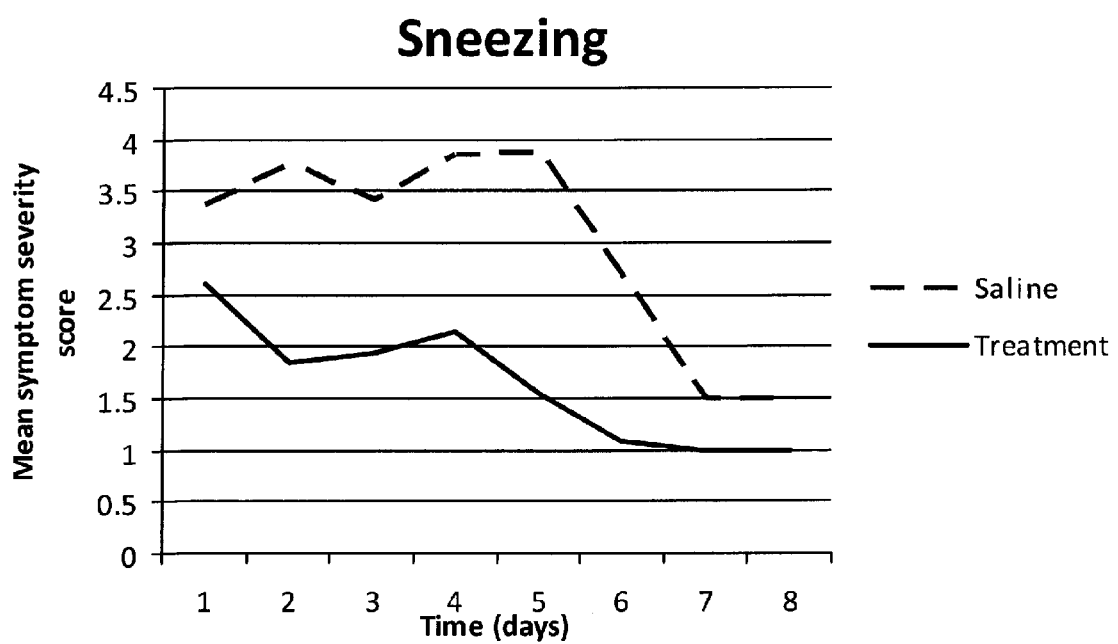
FIG. 1 is a graph illustrating the severity of sneezing experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.
Figure 2:
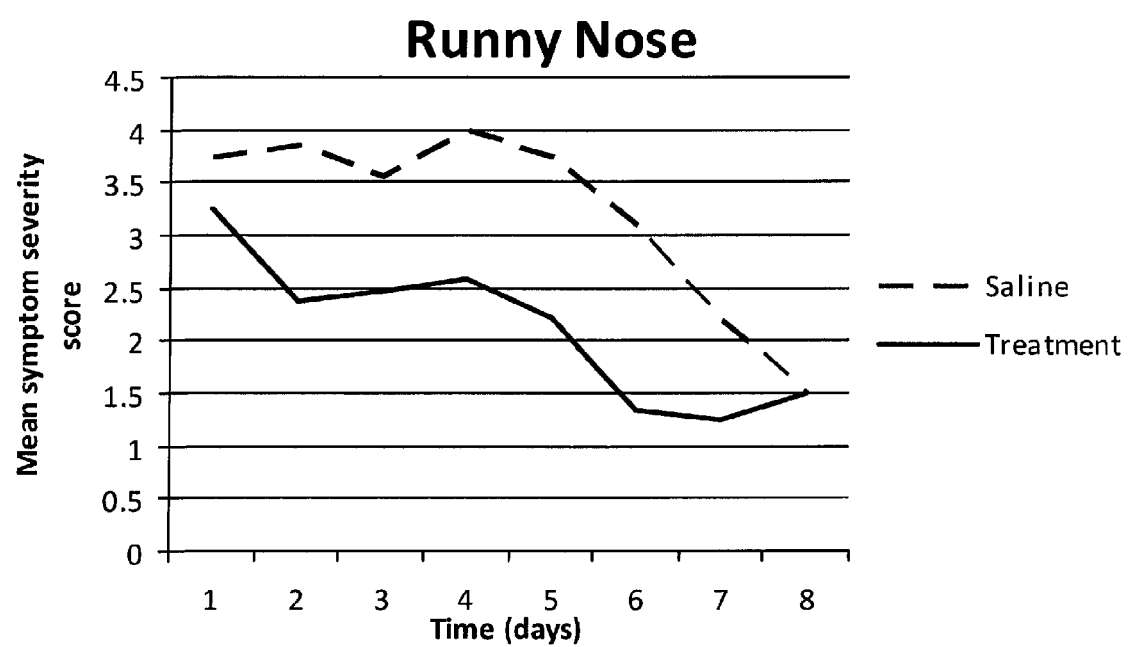
FIG. 2 is a graph illustrating the severity of runny noses experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.
Figure 3:
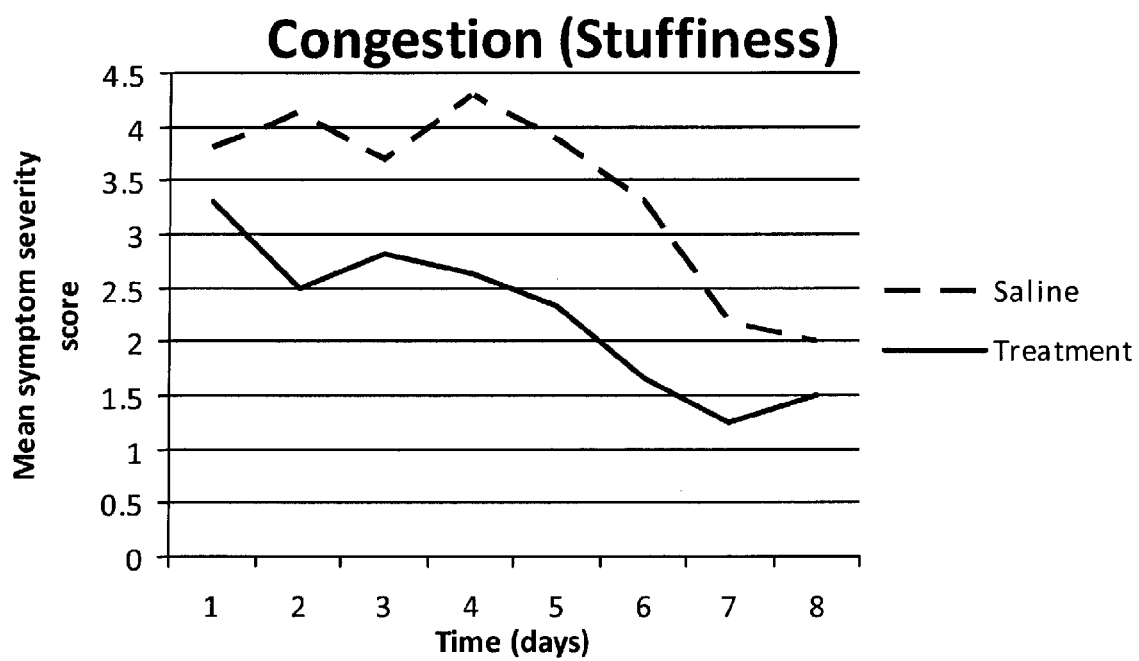
FIG. 3 is a graph illustrating the severity of congestion (stuffiness) experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.
Figure 4:
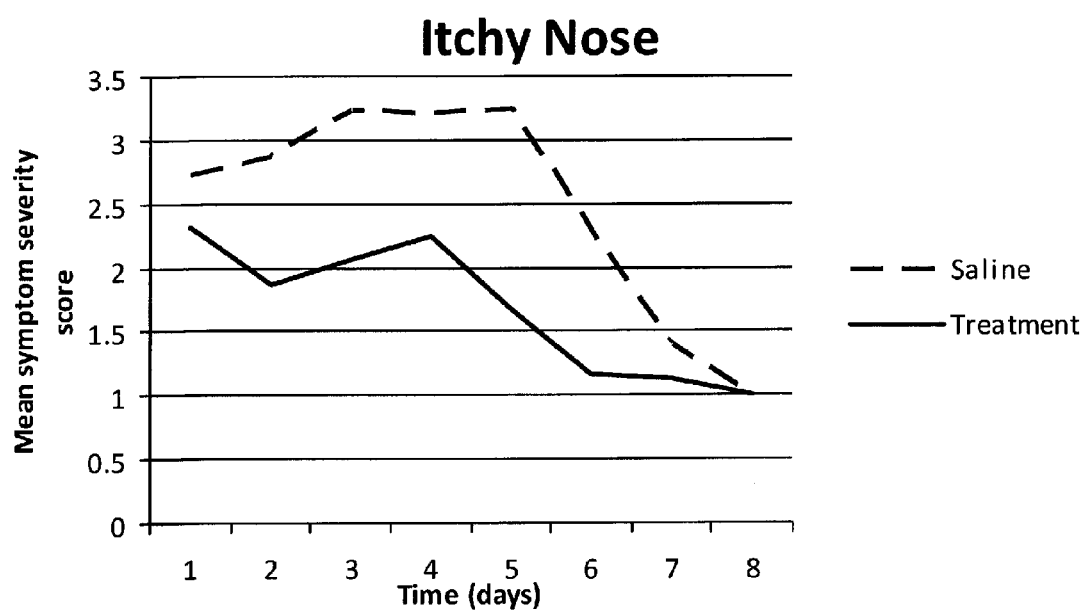
FIG. 4 is a graph illustrating the severity of itchy noses experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.
Figure 5:
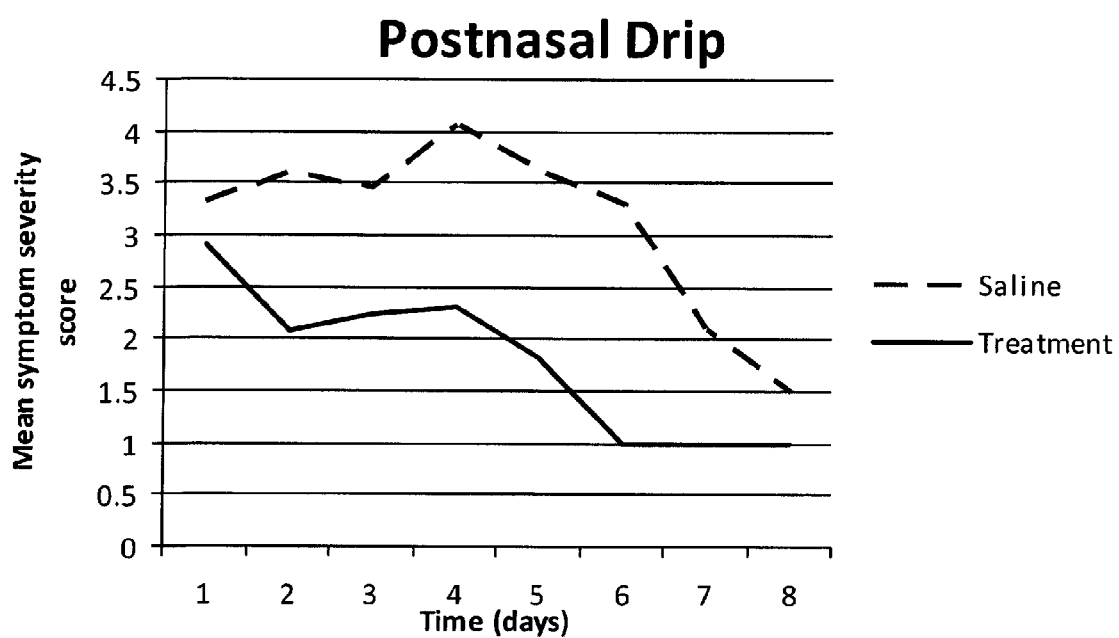
FIG. 5 is a graph illustrating the severity of postnasal drip experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.
Figure 6:
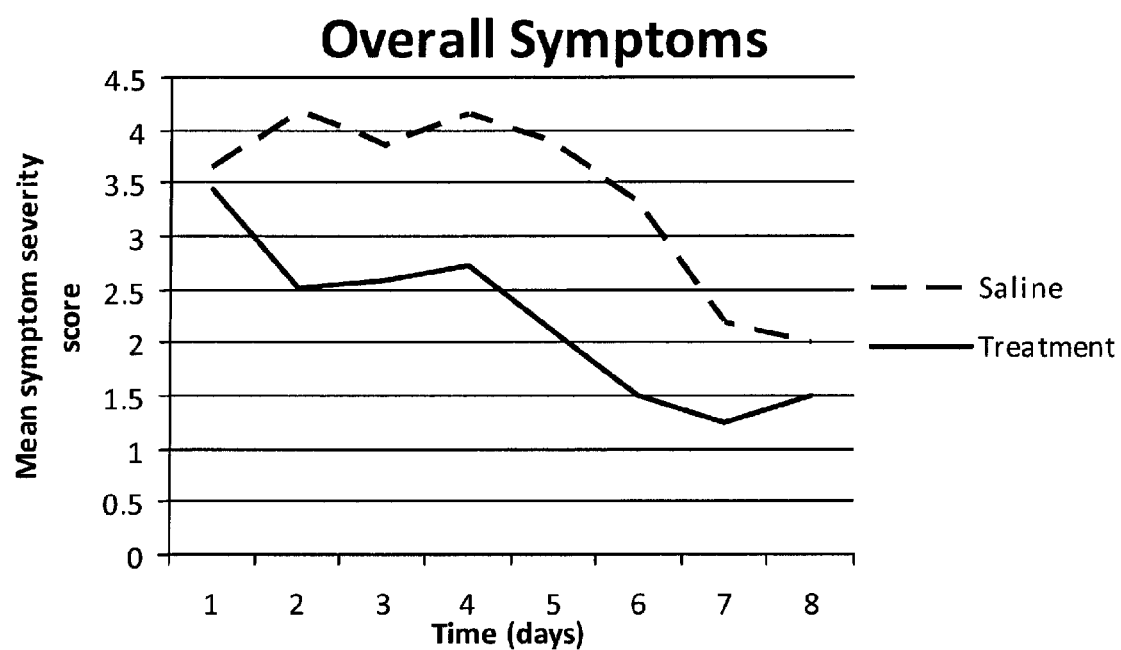
FIG. 6 is a graph illustrating the severity of overall cold symptoms experienced over time for persons treated with placebo (saline nasal spray) and for persons treated with a combination of a nasal steroid and a nasal antihistamine. The mean symptom severity score is based on the symptom severity scores given in the quality of life questionnaire associated with Study 2, described below.

This patent relates generally to the combination of a nasal steroid and a nasal antihistamine, and the use of this combination in treating VRTIs, URIs, or colds and in reducing the frequency in which colds (e.g., VRTIs, URIs) or cold symptoms are experienced.

There is herein provided a description of a product and method of treating the common cold, VRTIs, or URIs by using a combination of one or more nasal steroids with one or more nasal antihistamines. The products and methods described in this patent may be used in pediatric as well as adult treatment of colds, VRTIs, and URIs in humans.

More than 200 different viruses are known to cause VRTIs, URIs, and colds. Such viruses can include picornaviruses, coronaviruses, and respiratory syncytial virus ("RSV"). One use of the products and methods described in this patent is the treatment of VRTIs, URIs, or colds. For the purposes of this disclosure, all of the aforementioned viruses as well as any other viruses that might cause colds are collectively referred to as "rhinoviruses" because rhinoviruses are the most common VRTI-causing virus. These rhinoviruses generate an intense inflammatory response locally in the nose, and this inflammatory response constitutes cold symptoms, such as nasal congestion, sneezing, bronchial congestion, watery eyes, headaches, runny nose and a host of other varying symptoms, all of which are well known. Without these symptoms, VRTIs, URIs, or colds are little more than a benign viral infection causing little discomfort. As used in this patent, the term "resolution" as in "resolution of cold symptoms" refers to a reduction in the severity of cold symptoms so that they cause little or no discomfort to a person who is experiencing a cold (e.g., VRTI, URI) or has recently experienced a cold (e.g., VRTI, URI) or cold symptoms.

Nasal steroids are known in the art. Any nasal steroid will work suitably well in this invention, and examples of suitable nasal steroid sprays include flunisolide, fluticasone, Nasonex (mometasone), Becaonase AQ (beclomethasone), Flonase (fluticasone), Veramyst (fluticasone furoate), Nasocort AQ (triamcinolone), Rhinocort AQ (budesonide), Omnaris (ciclesonide), and Nasarel (flunisolide). Although one aspect of the present invention includes the use of a nasal steroid spray, the present invention may also include the use of other dosage forms of nasal steroids, including oral (e.g., pill, tablet, capsule), buccal, sublingual, orally-disintegrating, liquid solution or suspension, inhalational (aerosol, inhaler, nebulizer), parenteral injection, topical, or transdermal dosage forms.

Nasal antihistamines are also known in the art. Any nasal antihistamine will work suitably well in this invention, and examples of suitable nasal antihistamine sprays include Astelin (azelastine) and Patanase (olopatadine). Although one aspect of the present invention includes the use of a nasal antihistamine spray, the present invention may also include the use of other dosage forms of nasal antihistamines, including oral (e.g., pill, tablet, capsule), buccal, sublingual, orally-disintegrating, liquid solution or suspension, inhalational (aerosol, inhaler, nebulizer), parenteral injection, topical, or transdermal dosage forms.

Heretofore, nasal steroids and nasal antihistamines have been prescribed and used for the treatment of allergic rhinitis. Typically, either the nasal steroid or the nasal antihistamine alone is sufficient to treat the allergic rhinitis symptoms, although the treatment of severe allergic rhinitis occasionally calls for the prescription of both a nasal steroid and a nasal antihistamine. See, e.g., U.S. Pat. No. 6,858,596 col. 6, ll. 37-44 (filed Feb. 4, 2002). Although nasal steroids and nasal antihistamines have been prescribed to treat severe cases of allergic rhinitis, it was unexpectedly found that VRTIs, URIs, and colds may be effectively treated using a combination of a nasal steroid and a nasal antihistamine.

The combination of a nasal steroid with a nasal antihistamine as described in the present disclosure provides treatment of the common cold (e.g., VRTIs, URIs). By "combination," it is intended that the nasal steroid may be physically combined or mixed with the nasal antihistamine; the term "combination" includes any dosage form, including combination products, and including oral (e.g., pill, tablet, capsule), buccal, sublingual, orally-disintegrating, liquid solution or suspension, inhalational (aerosol, inhaler, nebulizer), parenteral injection, topical, or transdermal dosage forms. The preferred dosage form is a liquid solution or suspension containing an effective amount of both the nasal steroid and nasal antihistamine so that it may be sprayed into the nose. The term "combination" is also intended to include the concurrent or sequential use of a nasal steroid and a nasal antihistamine without actual combination or mixture of the nasal steroid and antihistamine—for example, where a patient first is administered a nasal steroid and sometime thereafter is administered a nasal antihistamine. The term "to administer" and its various tenses will be understood by one of ordinary skill in the art to include the administration a drug or medication, for example, according to label directions, done by the patient himself or herself, or by another person (e.g., a health care professional).

The term "treatment," as in the treatment of VRTIs, URIs, or colds using the products or methods described in this patent, refers to the administration of a drug or medication to achieve a reduction of the severity, duration, or frequency of the onset of symptoms (e.g., cold symptoms). The term "effective amount" will be understood by one of ordinary skill in the art to refer to a quantity in terms of concentration and mass sufficient to provide treatment.

Current cold treatments are palliative, in that they only mask cold symptoms but do not effectively reduce the duration of colds or cold symptoms. Likewise, current cold treatments do not effectively reduce the frequency with which colds or cold symptoms are experienced. As described more fully below, the administration of the treatments described in this patent show a marked reduction in the duration of a cold (or of cold symptoms), which confirms their surprising and unanticipated nature. For example, the administration of one of the tested combinations of a nasal steroid and a nasal antihistamine showed a reduction in the number of hours cold symptoms were experienced of approximately 50% compared to placebo, and the average efficacy across all tested combinations was 33% compared to placebo. Moreover, in addition to significantly reducing the severity of the cold symptoms experienced, the treatments described in this patent cause the person to whom the treatment is administered to experience cold symptoms at a much-reduced rate.

When a combination of one or more nasal steroids with one or more nasal antihistamines is administered to a patient, the patient's entire inflammatory response to the common cold is impeded or eliminated. The antihistamine blocks the histamine cascade via a selective inhibition of H1 receptors, while the nasal steroid blocks the inflammatory response by decreasing the influx of mast cells, Th2 lymphocytes, and eosinophil granulocytes. The unexpected synergism associated with the use of the combination of an antihistamine with a nasal steroid interrupts the inflammatory cascade, which significantly reduces cold symptoms or can be used to avoid cold symptoms.

It has been found that the use of both a nasal steroid and a nasal antihistamine in combination works significantly better than a nasal steroid or a nasal antihistamine by itself to block the entire range of the inflammatory response that produces symptoms of the common cold. Thus, the use of both a nasal steroid and a nasal antihistamine in combination effectively impedes the onset of the inflammatory response.

Preferably, the combination of a nasal steroid and a nasal antihistamine is administered within the first twenty-four to forty-eight hours after the onset of cold symptoms. Once a person begins using the combination, it has been found that most people experience results within about twenty-four hours. On average, a person to whom the combination has been administered ceases to experience any cold symptoms after approximately 80 hours, compared to approximately 119 hours with placebo. By blocking the inflammatory response, the VRTI is effectively rendered a benign viral infection causing little if any noticeable cold symptoms.

It has also been found that persons who are administered a combination of a nasal steroid and a nasal antihistamine have greater immunity from the symptoms of VRTIs, URIs, and colds. For example, as described in Study 1 below, persons to whom both a corticosteroid and an antihistamine were administered did not experience cold symptoms, or they experienced cold symptoms at a much reduced frequency as compared to the frequency at which they experienced cold symptoms prior to the administration of the corticosteroid and antihistamine combination.

Studies

In developing the combination and use of a nasal steroid and a nasal antihistamine, it was observed that persons to whom both a nasal steroid and a nasal antihistamine had been administered experienced cold symptoms (nasal congestion, sneezing, bronchial congestion, watery eyes, headaches, runny nose and a host of other varying symptoms, all of which are well known) at a much reduced rate as compared to when they were not administered the nasal steroid and nasal antihistamine. Further informal testing demonstrated that, where the patient was administered a combination of a nasal steroid and a nasal antihistamine within twenty-four hours of experiencing cold symptoms, the cold symptoms caused by the VRTI, URI, or cold were greatly diminished or resolved within about twenty-four hours after administration of the treatment.

Study 1

Forty patients to whom a combination of a nasal steroid and a nasal antihistamine had been administered provided information regarding the incidence of cold symptoms (nasal congestion, sneezing, bronchial congestion, watery eyes, headaches, runny nose and a host of other varying symptoms, all of which are well known) experienced during the time in which the combination was administered. The patients provided information regarding (1) the frequency with which they experienced cold symptoms while having been administered the nasal steroid/nasal antihistamine spray combination; (2) the frequency with which they experienced cold symptoms in a corresponding time frame during the prior year, during which time they were not being administered the nasal steroid/nasal antihistamine spray combination; (3) the duration of any cold symptoms experienced during the time period in which the patient had been administered the nasal steroid/nasal antihistamine combination; and (4) the duration of cold symptoms experienced during the prior year when the patient had not been administered the nasal steroid/nasal antihistamine combination.

Patients who suffered from chronic sinusitis were excluded from the pool of patients who were surveyed, as were patients who were immunosuppressed. Also, episodes of sinusitis were excluded from the responses of Questions 1 and 2.

Table 1 provides the results of Study 1. The forty patients surveyed had experienced a total of seventy-five colds (e.g., VRTIs, URIs) during the time period in which they had not been administered the nasal steroid/nasal antihistamine combination ("Year 1"). During the time in which they had been administered the nasal steroid/nasal antihistamine combination ("Year 2"), eleven of the forty patients experienced cold symptoms and twenty-nine experienced no cold symptoms. Of the eleven patients who experienced cold symptoms during Year 2, all experienced cold symptoms only once during Year 2. The eleven patients who had experienced cold symptoms during Year 2 had experienced a total of twenty-four colds during Year 1. On average, the eleven patients who experienced colds during Year 2 ceased experiencing cold symptoms within twenty-four hours after administration of the combination of a nasal steroid and a nasal antihistamine.

TABLE 1

Effectiveness of Treatment.

| | |
|---|---|
| Total number of patients | 40 |
| Total number of colds experienced in Year 1 | 75 |
| Number of patients who experienced cold symptoms in Year 2 | 11 |
| Total number of episodes of cold symptoms experienced in Year 2 | 11 |
| Average time of resolution of cold symptoms (following the onset of cold symptoms) | Less than 24 hours |
| Total number of episodes of cold symptoms experienced in Year 1 by patients experiencing cold symptoms in Year 2 | 24 |
| Patients without symptoms in year 2 | 29 |
| Colds contracted in year 1 | 53 |

The results of Study 1 demonstrate that the administration of a combination of a nasal steroid and a nasal antihistamine is effective to reduce the frequency with which a person experiences colds (e.g., VRTIs, URIs) or cold symptoms. Moreover, the results of Study 1 show that person to whom a combination of a nasal steroid and a nasal antihistamine has been administered and who does experience cold symptoms will experience those cold symptoms for a greatly reduced duration.

Study 2

A double blind placebo controlled multiple-arm study was done to further evaluate the efficacy of the use of a combination of a nasal steroid with a nasal antihistamine to treat and abort the common cold. A total of 250 patients (ages 18 to 72, with an average age of 43) were randomized to receive either the active combination (nasal steroid and nasal antihistamine) or placebo (saline solution). Table 2 summarizes the patients' demographics. Patients in the active combination arm were given one of the following active combinations: fluticasone and azelastine; fluticasone and olopatadine; fluticasone furoate and azelastine; fluticasone furoate and olopatadine; and mometasone and olopatadine. The placebo arm was given a nasal saline spray.

TABLE 2

Patient Demographics.

| Demographic | Group (N = 47) | | p value |
| --- | --- | --- | --- |
| | Placebo (n = 11) | Treatment (n = 36) | |
| Age (years) | 63 ± 18 | 62 ± 18 | 0.386 |
| Sex | | | 0.999 |
| Male (number) | 3 | 11 | |
| Female (number) | 8 | 25 | |

Excluded from the study were persons under the age of eighteen or who suffer from chronic allergies, chronic rhinitis, chronic sinusitis, take chronic allergy medications or chronic steroids, who are immunocompromised or who have a known allergy to antihistamines or steroids. Patients enrolled in the study were instructed to avoid the use of other over the counter cold medicine treatments during the study. The patients' other medications were reviewed prior to enrollment to avoid medication interactions.

Patients were enrolled in the study prior to the onset of cold symptoms and were randomly assigned to either the placebo arm or to the active combination arm. Patients in the active combination arm were assigned one of the specific combinations of a nasal steroid and a nasal antihistamine listed above. Patients were instructed to start the medication at the onset of common cold symptoms. Patients used two sprays of each medication intranasally with onset of cold symptoms (i.e., two sprays of the nasal steroid and two sprays of the nasal antihistamine assigned, or four sprays of saline spray, per the assigned arm) and continued with two sprays twice daily until cold symptoms were resolved.

Each patient completed a quality of life ("QOL") questionnaire for every cold episode that occurred during the study, in which the patient was able to rate the severity of cold symptoms experienced according to an objective set of criteria. Specifically, patients were able to note the severity of the following cold symptoms: sneezing, runny nose, congestion (stuffiness), itchy nose, postnasal drip, and overall symptoms. Patients rated the severity of each of these symptoms twice daily for eight days following the start of the administration of the combination of nasal steroid and nasal antihistamine. Patients rated the severity of these symptoms on a scale of 1 to 7, with 1 being the least severe and 7 being the most severe. A score of 1 was defined to mean "None—to an occasional limited episode;" a score of 3 was defined to mean "Mild—Steady symptoms but easily tolerable;' a score 5 of was defined to mean "Symptoms hard to tolerate, may interfere with activities of daily living or sleep;" and a score of 7 was defined to mean "Unbearably Severe—Symptoms are so bad, person can't function all the time."

Study 2 Results

Forty-seven participants in the study experienced cold symptoms during the study period and returned the QOL questionnaire. The data were analyzed comparing the total hours of cold symptoms, time from beginning treatment to resolution of cold symptoms, and symptom severity (for sneezing, runny nose, congestion, itchy nose, post-nasal discharge, and overall symptom severity). Of these 47 participants, 11 (23%) were in the placebo arm and 36 (77%) were in the treatment arm. Of the 36 participants in the treatment arm, 9 used Flonase-Patanase, 17 used Flonase-Astelin/Astepro, 7 used Veramyst-Patanase, 2 used Veramyst-Astelin, and 1 used Nasonex-Patanase. This breakdown of patients and treatment groups is summarized in Table 3. The mean age of the subjects was 43±15 years. Thirty-three (70%) of the participants were female.

TABLE 3

Breakdown of Patients and Treatment Groups.

| Medication | Number of Participants | Percent of Total |
| --- | --- | --- |
| Saline | 11 | 23.4 |
| Flonase (fluticasone) and Patanase (olopatadine) | 9 | 19.1 |
| Veramyst (fluticasone furoate) and Astelin (azelastine) | 2 | 4.3 |
| Flonase (fluticasone) and Astelin (azelastine) | 17 | 36.2 |
| Veramyst (fluticasone furoate) and Patanase (olopatadine) | 7 | 14.9 |
| Nasonex (mometasone) and Patanase (olopatadine) | 1 | 2.1 |
| Total | 47 | 100.0 |

The data showed no statistical differences attributable to age or gender. Both the placebo arm and the treatment arm began administration of the medication an average of 9 (±10) hours after the onset of cold symptoms.

Seventeen participants presented nasal swabs for viral identification. Six different virus profiles were identified: coronavirus 229E (4 participants), rhinovirus (4 participants), both coronavirus 229E and rhinovirus together (1 participant), coronavirus NL63 (1 participant), and RSV (1 participant). No virus was not detected in 6 of the participants' nasal swabs.

For 8 days following the onset of cold symptoms, the participants were observed for the presence of a variety of typical cold symptoms, including congestion, itchy nose, runny nose, postnasal discharge, and sneezing. The total hours of cold symptoms and total hours from the beginning of treatment to resolution of cold symptoms were surprisingly significantly less in the active combination arm compared to the placebo arm. The mean total hours of cold symptoms in the active combination arm was 80.39 (±59.4), as compared to 118.91 (±45.6) for the placebo arm. The mean hours from the beginning of treatment to resolution of the cold symptoms was 71.06 (±60.4) for the active combination arm, compared to 110.55 (±47.7) for the placebo arm.

The data were also analyzed and statistically compared to placebo for each specific nasal steroid/nasal antihistamine combination tested. Table 4 lists mean total hours of cold symptoms experienced with each treatment combination, as well as the mean total hours of cold symptoms experienced with placebo. Table 4 also includes the mean hours from the beginning of treatment to the resolution of cold symptoms for each treatment combination, as well as the mean hours from the beginning of treatment to the resolution of cold symptoms in the placebo group.

TABLE 4

Duration of Cold Symptoms (in Total and Following Start of Treatment).

| Treatment Used | | Total Cold (hrs) | Treatment Start to Cold Stop (hrs) |
|---|---|---|---|
| Saline | Mean | 118.91 | 110.55 |
| N = 11 | Median | 122.00 | 102.00 |
| | Mode | 57[a] | 57 |
| | Std. Deviation | 45.619 | 47.704 |
| | Range | 140 | 140 |
| | Minimum | 57 | 52 |
| | Maximum | 197 | 192 |
| Fluticasone and | Mean | 59.89 | 47.22 |
| olopatadine | Median | 41.00 | 36.00 |
| N = 9 | Mode | 20[a] | 11[a] |
| | Std. Deviation | 37.863 | 38.935 |
| | Range | 116 | 125 |
| | Minimum | 20 | 11 |
| | Maximum | 136 | 136 |
| Fluticasone furoate | Mean | 74.50 | 61.50 |
| and azelastine | Median | 74.50 | 61.50 |
| N = 2 | Mode | 40[a] | 36[a] |
| | Std. Deviation | 48.790 | 36.062 |
| | Range | 69 | 51 |
| | Minimum | 40 | 36 |
| | Maximum | 109 | 87 |
| Fluticasone and | Mean | 103.71 | 95.53 |
| azelastine | Median | 97.00 | 96.00 |
| N = 17 | Mode | 9[a] | 36[a] |
| | Std. Deviation | 73.025 | 74.712 |
| | Range | 279 | 274 |
| | Minimum | 9 | 2 |
| | Maximum | 288 | 276 |
| Fluticasone furoate | Mean | 58.43 | 50.57 |
| and olopatadine | Median | 46.00 | 37.00 |
| N = 7 | Mode | 26[a] | 21[a] |
| | Std. Deviation | 31.010 | 30.010 |
| | Range | 79 | 73 |
| | Minimum | 26 | 21 |
| | Maximum | 105 | 94 |
| Mometasone and | Mean | 34.00 | 32.00 |
| olopatadine | Median | 34.00 | 32.00 |
| N = 1 | Mode | 34 | 32 |
| | Range | 0 | 0 |
| | Minimum | 34 | 32 |
| | Maximum | 34 | 32 |
| Total for all | Mean | 80.39 | 71.46 |
| active combinations | Median | 60.00 | 44.50 |
| N = 36 | Mode | 34[a] | 36 |
| | Std. Deviation | 59.417 | 60.494 |
| | Range | 2790 | 274 |
| | Minimum | 9 | 2 |
| | Maximum | 288 | 276 |

[a]Multiple modes exists. The smallest value is shown.

Figure 7:
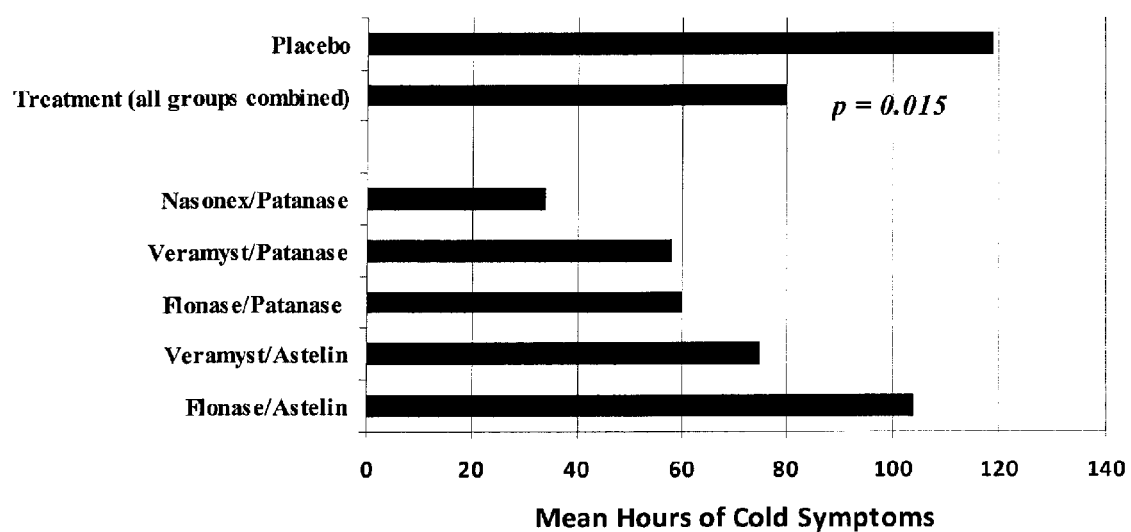
FIG. 7 is a graph illustrating the mean number of hours in which patients in Study 2, described below, experienced cold symptoms. The graph shows the mean number of hours of cold symptoms experienced by patients in each of the treatment groups studied, in all treatment groups combined, and in the placebo group.
Figure 8:
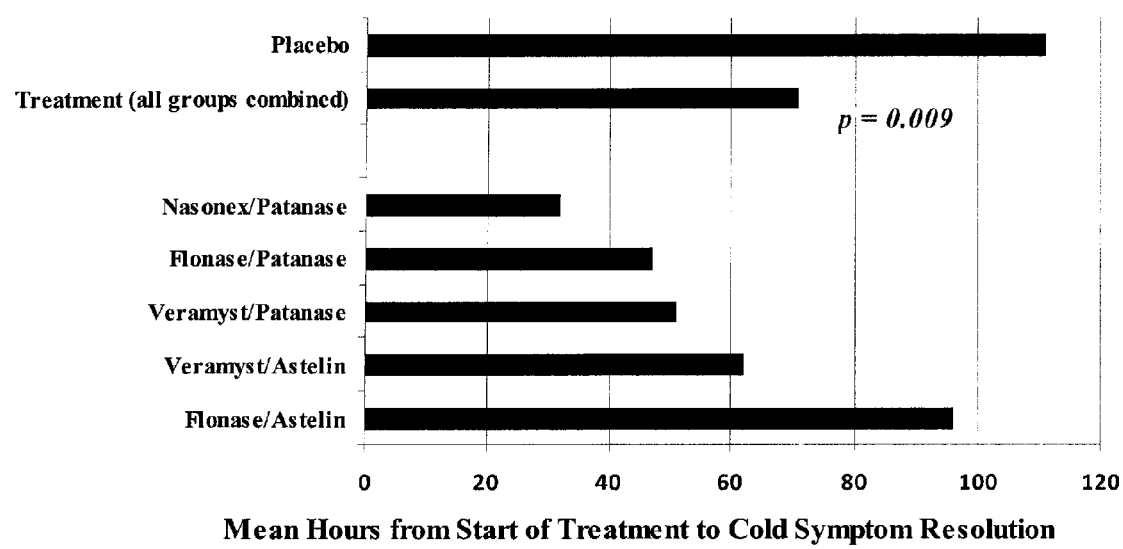
FIG. 8 is a graph illustrating the mean number of hours from the beginning of treatment to the resolution of cold symptoms experienced by patients in Study 2, described below. The graph shows the mean number of hours from the beginning of treatment to the resolution of cold symptoms experienced by patients in each of the treatment groups studied, in all treatment groups combined, and in the placebo group.

The results of Study 2, which are contained in Table 4, are also illustrated in FIG. 7 and FIG. 8. FIG. 7 illustrates that the use of any of the combinations of a nasal antihistamine and a nasal steroid studied significantly reduces the number of hours of cold symptoms experienced, compared to placebo. FIG. 8 shows that the use of any of the combinations of a nasal antihistamine and a nasal steroid studied significantly reduces the number of hours between the patients' beginning of treatment to the resolution of the patients' cold symptoms. These data demonstrate that treatment of a combination of an nasal antihistamine and a nasal steroid, administered near the onset of cold symptoms, significantly reduces the duration of the cold symptoms. In general, these data demonstrate conclusively that the treatment, no matter what treatment was tried, successfully reduced the cold symptoms' duration and severity.

Data was analyzed daily to assess symptoms of sneezing, runny nose, congestion, itchy nose, post-nasal discharge, and overall symptom severity. This data regarding symptom severity was gathered from the QOL questionnaire outlined above. FIGS. 1 through 6 illustrate the markedly decreased severity of cold symptoms experienced with the treatment, as compared to placebo. In each Figure, the values on the X-axis represent the time in days, and the values on the Y-axis represent the averages of the patient's assessment of the severity of their respective cold symptoms using a scale of 1 to 7, as outlined above.

The results of Study 2 confirmed that the administration of a combination of a nasal steroid and a nasal antihistamine is remarkably effective to reduce duration and severity of cold symptoms. The total hours of cold symptoms experienced by the patient and the hours of treatment required were significantly reduced by the use of the combination of nasal steroid and nasal antihistamine as compared to placebo. Likewise, the severity of symptoms was greatly reduced by the use of the combination of a nasal steroid and a nasal antihistamine on every day cold symptoms were experienced, as compared to placebo. This conclusion was true for every specific combination tested, and unequivocally supports the conclusion that the general use of a nasal steroid with a nasal antihistamine will be an effective treatment for a cold (e.g., VRTI, URI) or cold symptoms.

Benefits

There are numerous potential benefits of the present invention. In the short term, a suitable nasal steroid can be combined with a suitable nasal antihistamine to provide effective treatment for VRTIs, URIs, or colds. For example, this combination can be carried in small quantities (e.g., a few days' worth of medication) in order to treat an individual episode of the common cold on the spot. This will allow a person to remain ready to begin treatment immediately upon the onset of VRTI symptoms.

Not only would this combination present a cost-effective treatment of VRTIs, but by curing common cold symptoms it would present economic and personal benefits in terms of avoiding the annual onslaught of colds (e.g., VRTIs, URIs) associated with cold season.

Although other modifications and changes may be suggested by those skilled in the art, it is the intention of the inventors to embody within the patent warranted hereon all changes and modifications as reasonably and properly come within the scope of their contribution to the art.

I claim:

1. A method of treating viral upper respiratory infections, said method consisting essentially of administering nasally an effective amount of one or more steroids and an effective amount of one or more antihistamines.

2. The method of claim 1, wherein the one or more steroids are selected from the group consisting of flunisolide, fluticasone, mometasone, beclomethasone, fluticasone furoate, triamcinolone, budesonide, and ciclesonide;
and wherein the one or more antihistamines are selected from the group consisting of azelastine and olopatadine.

3. The method of claim 1, wherein the one or more steroids have a dosage form consisting of nasal sprays;
and wherein the one or more antihistamines have a dosage form consisting of nasal sprays.

4. The method of claim 1, wherein the one or more steroids and the one or more antihistamines have been combined in a dosage form.

5. The method of claim 1, wherein the one or more steroids and the one or more antihistamines have been combined in a nasal spray.

6. The method of claim 1, wherein the one or more steroids comprises fluticasone furoate, and wherein the one or more antihistamines comprises olopatadine.

7. A method of reducing a frequency of viral upper respiratory infections, said method consisting essentially of administering nasally an effective amount of one or more steroids and an effective amount of one or more antihistamines.

8. The method of claim 7, wherein the one or more steroids are selected from the group consisting of flunisolide, fluticasone, mometasone, beclomethasone, fluticasone furoate, triamcinolone, budesonide, and ciclesonide;

and wherein the one or more antihistamines are selected from the group consisting of azalastine and olopatadine.

9. The method of claim 7, wherein the one or more steroids have a dosage form consisting of nasal sprays;

and wherein the one or more antihistamines have a dosage form consisting of nasal sprays.

10. The method of claim 7, wherein the one or more steroids and the one or more antihistamines have been combined in a dosage form.

11. The method of claim 7, wherein the one or more steroids and the one or more antihistamines have been combined in a nasal spray.

12. The method of claim 7, wherein the one or more steroids comprises fluticasone furoate, and wherein the one or more antihistamines comprises olopatadine.

13. The method of claim 1, wherein the one or more steroids are selected from the group consisting of flunisolide, fluticasone, mometasone, beclomethasone, fluticasone furoate, triamcinolone, budesonide, and ciclesonide.

14. The method of claim 1, wherein the one or more antihistamines are selected from the group consisting of azelastine and olopatadine.

15. The method of claim 1, wherein the one or more steroids have a dosage form consisting of a nasal spray.

16. The method of claim 1, wherein the one or more antihistamines have a dosage form consisting of a nasal spray.

17. The method of claim 7, wherein the one or more steroids are selected from the group consisting of flunisolide, fluticasone, mometasone, beclomethasone, fluticasone furoate, triamcinolone, budesonide, and ciclesonide.

18. The method of claim 7, wherein the one or more antihistamines are selected from the group consisting of azelastine and olopatadine.

19. The method of claim 7, wherein the one or more steroids have a dosage form consisting of a nasal spray.

20. The method of claim 7, wherein the one or more antihistamines have a dosage form consisting of a nasal spray.

\* \* \* \* \*